(12) United States Patent
Korigodskiy et al.

(10) Patent No.: US 10,130,509 B2
(45) Date of Patent: Nov. 20, 2018

(54) DRAINAGE DEVICE AND METHOD OF PRODUCING SAME

(75) Inventors: Aleksandr Robertovich Korigodskiy, Moscow (RU); Igor Borisovich Alekseev, Moscow (RU); Sergey Sergeevich Dolgiy, Moscow (RU); Aleksey Yurievich Slonimskiy, Moscow (RU)

(73) Assignee: Ivan Dmitrievich Zakharov, Moscow (RU)

( * ) Notice: Subject to any disclaimer, the term of this patent is extended or adjusted under 35 U.S.C. 154(b) by 975 days.

(21) Appl. No.: 14/394,010

(22) PCT Filed: Apr. 12, 2012

(86) PCT No.: PCT/RU2012/000278
§ 371 (c)(1),
(2), (4) Date: Feb. 9, 2015

(87) PCT Pub. No.: WO2013/154450
PCT Pub. Date: Oct. 17, 2013

(65) Prior Publication Data
US 2015/0157504 A1    Jun. 11, 2015

(51) Int. Cl.
*A61M 5/00* (2006.01)
*A61F 9/007* (2006.01)

(52) U.S. Cl.
CPC .. *A61F 9/00781* (2013.01); *A61F 2210/0004* (2013.01); *A61F 2230/0067* (2013.01); *A61F 2240/00* (2013.01); *A61F 2240/001* (2013.01)

(58) Field of Classification Search
CPC .......... A61F 9/00781; A61F 2210/0004; A61F 2230/0067; A61F 2240/00; A61F 2240/001
See application file for complete search history.

(56) References Cited

U.S. PATENT DOCUMENTS 6,375,642 B1 * 4/2002 Grieshaber ......... A61F 9/00781
604/294

* cited by examiner

Primary Examiner — Philip R Wiest
(74) Attorney, Agent, or Firm — Florek & Endres PLLC

(57) ABSTRACT

The invention relates to medical technology and is intended for use in ophthalmology in the surgical treatment of various types of glaucoma. According to a first aspect of the invention, the drainage device for use in the surgical treatment of glaucoma is formed from a bioresorbable material in the form of a hollow profile with a closed contour in cross section, ensuring the possibility of the scleral flap passing through the cavity of the device during the surgical treatment. As a result, the formation of adhesions under the scleral bed, along the scleral flap rib and also between the scleral flap and the conjunctiva is prevented, the ease and reliability of fixing the device on the scleral flap is increased, and adverse immune and inflammatory reactions are reduced. According to a second aspect, the described drainage device is produced by manufacturing a blank from polymer material on a rod in the form of a hollow profile of closed cross section and subsequently cutting at least one section out of the blank in order to produce at least one drainage device. According to a third aspect of the invention, in order to produce the drainage device, a blank in the form of a hollow profile of closed cross section is woven from threads, and at least one section is subsequently cut out of the blank in order to produce at least one drainage device. According to a fourth aspect of the invention, blanks in the form of strips are produced from a flat preliminary blank made of polymer material, wherein the drainage device is produced by connecting the ends of at least one blank.

25 Claims, 4 Drawing Sheets

DRAINAGE DEVICE AND METHOD OF PRODUCING SAME

TECHNICAL FIELD

The invention relates to medical equipment, particularly, to the devices, used in ophthalmic surgery.

STATE OF ART

Glaucoma represents a large group of eye diseases with typical disturbances of visual functions. In many cases refuse of surgery or delay in its performing leads to the progressive decline in visual functions and to blindness. Fistulizing operations allow to create new ways of aqueous humor outflow from the eye.

Traditional operation of choice for surgical treatment of glaucoma is valvular sinus trabeculectomy with basal iridectomy, described, for instance, in A. P. Nesterov. Glaucoma, $2^{nd}$ edition, revised, M, 2008. During the operation, produce arcuate incision of the conjunctiva and Tenon's capsule in 7-8 mm from the limbus. Separate the Tenon's capsule from the sclera to the limbus. Cut out the limbus-based superficial scleral flap. Sizes of the flap vary from 3 to 5 mm with the thickness by ⅓ to ½ of the thickness of sclera. Separate the scleral flap from the lamina fusca sclera till the transparent corneal tissue, and depending on its shape put 1 or 2 stitches into the edge of the flap. Excise the area of the deep corneoscleral layer; the incision is made parallel to the limbus through the entire width of the scleral pocket. Second analogical incision is made by 1.0-1.5 mm anteriorly from the first one in the corneal part of the subscleral pocket. Then excise the area of the deep corneoscleral tissue between two described incisions. Perform peripheral iridectomy through the defect which was formed. Put the nodal stitches into the scleral flap. Complete the operation with careful suturing the wound of the conjunctiva.

Modification of trabeculectomy, the method of surgical treatment of glaucoma in also known (the patent RU No 22181273, 20 Apr. 2002 Erichev V. P., Bessmertniy A. M., Lobanov L. B., Chervyakov A. Y). The operation is performed as follows. In the upper quadrant of the eyeball separate the limbus-based conjunctival flap. Form the limbus-based superficial flap of sclera by ½ of its thickness, 4*4 mm in size. Suture with the zigzag stitch the side edges of the scleral bed. In the limbal area cut out a strip of the sclera with the trabecular tissue. Carry out the basal iridectomy. Perform the reposition of the scleral flap with two nodal stitches and the conjunctival flap, with the continuous suture.

In addition the variant of surgical treatment on the basis of non-penetrating deep sclerectomy, the method of surgical treatment of the secondary open-angle glaucoma was contrived (the patent RU No 22360657, 10 Jul. 2009, Takhchidi H. P., Cheglakov V. Y., Citov G. A., Valuev L. I., The method of surgical treatment of the secondary open-angle glaucoma). The method is carried out as follows. Perform cutting out of the conjunctival and superficial flaps, removal of middle layers of the sclera in the form of rectangle till the internal layers of the corneoscleral part of the trabecula and the limbal edge of the Descemet's membrane and drainage of the scleral space with the hydrophilic drainage, containing the covalently-bounded immobilized recombinant prourokinase; then perform the superficial scleral flap fixation in the angles. Complete the operation with continuous suture of the conjunctiva.

However, in some patients in different terms after the operation the cicatrical blockage in the area of the scleral flap and the filtering bleb with decrease of the hypotensive effect are developed.

To decrease the likelihood of such complication modification of the operation of surgical treatment of glaucoma with use of the drainage device was contrived. (The patent RU No 22348386, 10 Sep. 2008, Batmanov Y. E., Shvets P. N. The method of non-penetrating surgical treatment of the primary open-angle glaucoma). This operation was carried out as follows. Form the limbus-based conjunctival flap (10 mm in length) in 7 mm form the limbus. After the sparing coagulation of episcleral vessels outline the superficial scleral four-square flap with the 5 mm side, by ⅓ of the thickness; then separate it till the transparent corneal layers. Then outline three sides of the deep scleral flap of the rectangle shape 4*3 mm in size (notably, the lateral sides of the rectangle are 3 mm in length, perpendicular to the limb, and the long side is 4 mm in length), connecting them and locating 2 mm behind the scleral spur. Separate the deep scleral flap across the entire thickness of the sclera. Thus, open the venous sinus of the sclera. Remove the deep scleral flap with the Vannas scissors. If the filtration through the trabecula is absent, perform the removal of endothelium and juxtacanalicular tissue from its surface. Then under the superficial sclera flap place the thin collagen drainage 6*2 mm in size; its ends overhang the borders of the sclera flap. Fix the superficial sclera flap to the sclera with two nodal stitches. Put the continuous suture into the conjunctiva. The drainage device, used in the known method of treatment, is selected as the closest analogue.

There are disadvantages of the known method of treatment and the drainage device, particularly, in the early postoperative period there is the contact between the scleral flap and conjunctiva, which usually leads to the formation of scleral-conjunctival adhesions as well as scleral-scleral adhesions along the edge of the scleral flap; it decreases the effectiveness of the provided treatment. Besides, natural collagen (the material for producing the drainage) is characterized by the extra-slow resorption, which may cause inflammatory and other adverse reactions of the organism.

NATURE OF THE INVENTION

In consideration of the foregoing there is the task to create the drainage device, used in the surgical treatment of glaucoma, which would allow to prevent the formation of the scleral-scleral and conjunctival-scleral adhesions. The additional task is to create the drainage device, which would be characterized by the minimal immune reactions of the organism, greater biological compatibility, than the known analogues on the prior art. Another task is to create the relatively universal drainage device, which might be used in different types of glaucomatous operations.

The drainage device, used in the surgical treatment of glaucoma, made from the bioresorbable material as the complete profile with the closed circuit in the cross-section to make it possible to pass the sclera flap through the cavity of the device during the process of surgical treatment.

In the particular case, drainage device is manufactured in the form of a thin-walled tube with the outer surface as a part of tubular or conical surface. The thin-walled tube can be fit flat in rectangular plan with 4.0-6.0 mm in width and 1.5-3.5 mm in height, or trapezoidal form with larger base of trapezoid 4.0-6.0 mm, smaller base 2.5-5.5 mm, 1.5-3.5 mm in height, and a thickness of the device is 10-500 μm.

The device is preferably made from a film—blind, porous, at least punched fractionally. Device wall can be also made from a grid from bioresorbable material.

Synthetic polymers or microbiologically synthesized material can be used as bioresorable materials.

Synthetic polymer can be chosen from the following group: polyglycolic acid (polyglycolide), L- or D,L-polylactic acid (polylactide), poly-ε-caprolactone, poly-p-dioxanone, copolymers of these materials, mixes of these materials and/or copolymers.

Synthetic polymer can be made as a polyvinyl alcohol hydrogel or a graft-copolymer with polyvinyl alcohol and polyethylene glycol hydrogel.

One of the following material can be used as a microbiologically synthesized material: poly-3-hydroxybutyrate, poly-3-hydroxyvalerate or poly-4-hydroxybutyrate or their copolymers. Fused spider web proteins spidroin-1 and spidroin-2 can also used as microbiologically synthesized materials.

According to following aspects of the invention methods for the production of the drainage device have been proposed.

According to a first configuration, a blank from polymer material is manufactured on a rod in the form of a hollow profile of closed cross section, and at least one section is subsequently cut out of the blank in order to produce at least one drainage device.

A blank is manufactured by pouring from polymer solution. In one case, a blank wall, or a device wall is perforating fractionally.

In another case, a blank is made by pouring from polymer material with water-soluble ingredient. Then a blank is dried, a filler is washed off and at least one section is subsequently cut out of the blank.

In another method of manufacturing a tube with latticed wall is taking a thread up and subsequent baking.

According to another configuration, a blank in the form of a hollow profile of closed cross section is woven from threads, and at least one section is subsequently cut out of the blank in order to produce at least one drainage device.

According to a next configuration, blanks in the form of strips are produced from a flat preliminary blank made of polymer material, wherein the drainage device is produced by connecting the ends of at least one blank.

In one case a blank in the form of sheet is manufactured from polymer solution. In another case a blank in the form of sheet is poured from polymer solution with water-soluble ingredient, then a blank is dried and a filler is washed off to produce a porous sheet blank.

A lattice from bioresorbable threads is also used as a blank.

Drainage device is produced by connecting the ends of one or more blanks by a high-temperature welding, or gluing, or splicing.

Drainage device is formed in the form of a hollow profile with a closed contour in cross section. This form of drainage prevents the formation of adhesions under the scleral bed, along the scleral flap rib and also between the scleral flap and the conjunctiva. As a result, intraocular tension annealing is achieved, the result is kept for a significant period of time and probability of new surgical procedures is decreased.

This type of drainage devices is better to adjustment and use in comparison with other drainages. Its construction provides ease of installation and clamping on a scleral flap without extra clamping by thread. The construction described allows to use the device both in penetrative antiglaucomatous surgery and nonpenetrating deep scleroticectomy and its modifications.

Bioresorbable polymer materials using provides absence of expanding and pressure on tissues, size stability, drainage strength and biocompatibility (bioinertness) without immune or inflammatory response. Drainage resorbs completely in optimum time 3-6 months, which provides to form physiologically correct outflow tracts for aqueous humor and prevents progression postoperative hypotension.

BRIEF DESCRIPTION OF DRAWINGS

The invention is described in more detail with a reference to the schedule of drawings.

MOST PREFERRED EMBODIMENT OF THE INVENTION

Figure 1:
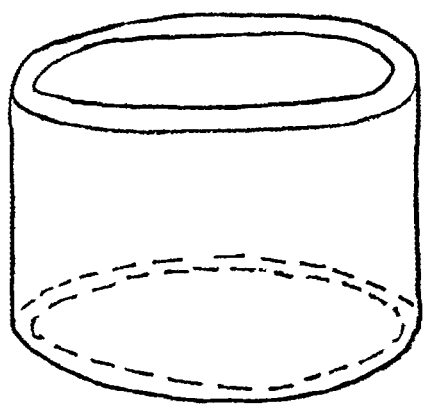
FIG. 1—drainage device with tubular side wall made from continuous film.
Figure 2:
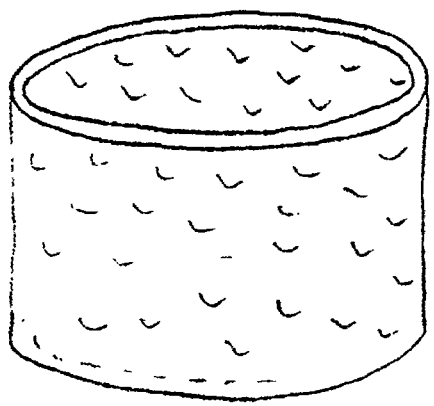
FIG. 2—drainage device with tubular side wall made from porous film.
Figure 3:
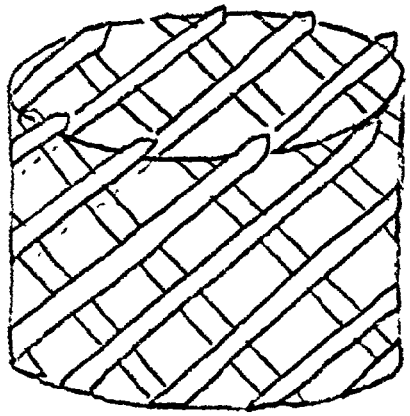
FIG. 3—drainage device with tubular side wall made from bioresorbable lattice.
Figure 4:
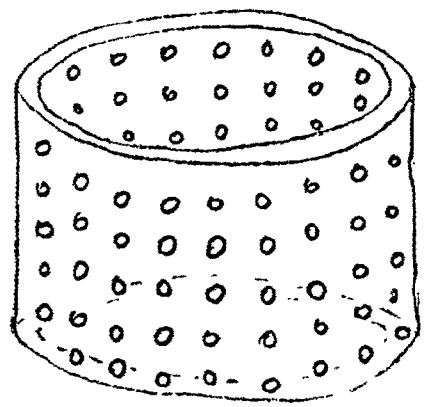
FIG. 4—drainage device with tubular side wall made from perforated film.
Figure 5:
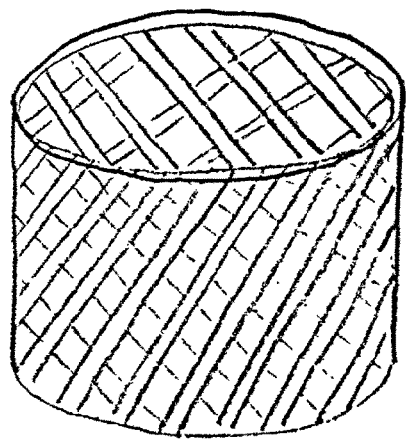
FIG. 5—drainage device with tubular side wall woven from bioresorbable lattice.

Drainage device has the form of a hollow profile of closed cross section with an appropriate (but unessential) tubular (with similar bases, FIG. 1) or conical (with various lower and upper base, FIG. 10) form of side wall. This preferred form of drainage device provides the ease of fixing the device on the scleral flap (with triangle or trapezoid form), and the best running of antiglaucomatous drainage in a body. The device can be flattened in a rectangular or trapezoidal plan for packaging and storage convenience.

Appropriate form and shape of the device can be selected with regard to form and shape of scleral flap, dissected out on surgery (trapezoid, lower base 4-5 mm, upper base 2-3 mm, trapeze height 4-5 mm). Therefore most preferable sizes are chosen from the following range:

for rectangle in plan: width: 4.0-6.0 mm, preferably, 4.5-5.5 mm for trapezoid: larger base: 4.0-6.0 mm, preferably, 4.5-5.5 mm; smaller base: 2.5-5.5 mm, preferably, 3.5-4.5 mm height (offcut length): 1.5-3.5 mm, preferably, 2.0-2.5 mm thickness: 10-500 μm, preferably, 50-100 μm.

Total thickness is composed of both wall thickness (original film or lattice). However, appropriate thickness can have different values for various variants of drainage.

It should be noted, that device design and method for production makes it possible to get the device with customized size, in spite of appropriate sizes, mentioned above, except that can be done by surgeon during a surgery (for a final drainage devise height simulation). Width of flat fitted drainage device (b) and diameter of original tube are in the ratio, according to a following equation: b=πd/2.

The device is made from bioresorbable (resolved) material, which can be continuous or discontinuous, according to the invention. Using of discontinuous material is more preferably, because pores and hollows provides more effective penetration of ocular fluid and better drain effect in general. Within of context of the invention different variants of discontinuous material are considered: porous film, perforated film, lattice. However, these variants are not restricted.

In general, a drainage device is manufactured by two primary ways. According to a first method, a thin-walled tube or cone is made from bioresorbable material, and then pieces (ring) of the plain blank are cut out square with lengthwise tube axis. A cone shaped blank is less preferable, because it allows to make only one device with required size. All of blanks mentioned above can be manufactured be casting from polymer solution, or assembling or weaving from threads.

According to a second method, prefabricated blanks are used: flat sheets made from continuous, porous or perforated film or lattice. Stripes (for example, rectangular) with a width, which is equal to drainage height, are cut out from sheets. Then short blanks in rectangular or trapezoid form are cut out from every stripe. Next, ends of these blanks are connected into drainage by alloying, gluing or piecing by bioresorbable thread. Drainage device is produced by connecting the ends of one or more blanks.

Porous film is produced by adding a leachable component (porophore) into a polymer solution. This inert additive (organic or inorganic) is removed completely from solid material by hydrowash at designed temperature due to a water solubility. Pore size and total porosity are depended on porophore particle size and concentration (in relation to polymer content). This kind of blank films can be manufactured in the plane mode (with subsequent cutting out and welding) or in the form of thin-walled tube.

Nontoxic porophores and flexibilizers are also used, and additive removing is processed into a body after device implantation.

Total porosity is defined as relation between pore volume and total volume of material. It can be calculated by the following equation:

$$P=(1-D/D_o)*100\%,$$

where D—apparent density of porous material, kg/m³, $D_0$—raw polymer density, kg/m³.

Appropriate value of total porosity is 70-85%. Strength and deformation parameters (disruptive strength, failure elongation) decreases at P>90% and as a result device destruction is taken place in implantation and service. Device filtering property decreases at P<25% because of closed pores formation and the rigidity increases leading to traumatizing of eye tissues. The mentioned above applies to drainage produced by porophore hydrowashing. For perforated film and lattices using term "porophore" is nominal and a real value of porosity may be more than 90% and mechanical characteristics of drainage may have be at good value.

Continuous film perforation is carried out by special perforating machine, for example dermatome (for making cross-cuts on a temporary vulnerary coating) or by laser micromachining of film materials. Pores produced by this method are 20-2000 μm in diameter. Perforation can be carried out both on prefabricated blanks (continuous films or thin-walled tubes) and devices. First variant is more preferable because of blank clamping.

Device can be manufactured from prefabricated lattice, woven in a shape of hose with diameter calculated by the formula mentioned above, or in a plane form (next ends of a sheet are welded). Lattice thickness is 10-500 μm (this value is 4 times more than thread diameter because of subbing in assemblies) 50-100 μm preferably, and an average diameter of pores is 50-1000 μm.

Device can be manufactured from bioresorbable threads, too. According to this method, threads are wound on a special rod and then baked. Thread diameter is 4-250 μm, preferably 20-40 μm.

Connection of blank stripes is carried out by high-temperature welding, gluing, splicing. Welding accessories for polymer film welding are used for high-temperature welding. Cyanoacrylate adhesives (glue for local uses and medical glue with fast UV-drying process) are used for gluing. Various kinds of resorbable surgical threads with a high strength and guarantee-covered period of biodestrucion are used for hand-operated splicing.

Figure 6:
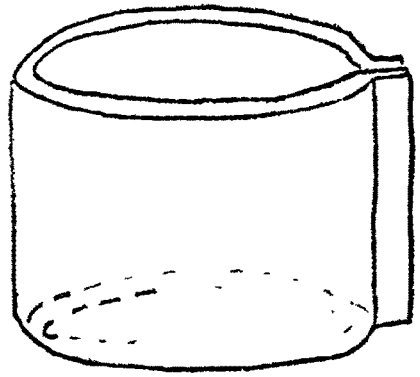
FIG. 6—drainage device made from a blank in the form of strip by connecting the ends.
Figure 7:
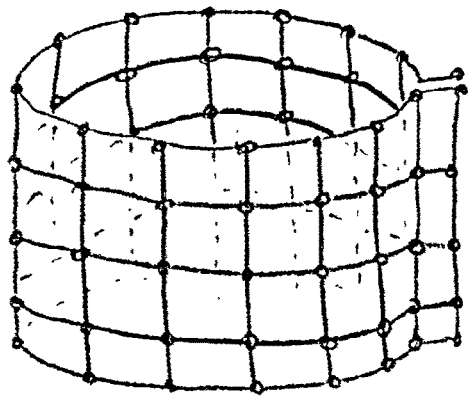
FIG. 7—the same as FIG. 6 with side wall made from lattice.
Figure 8:
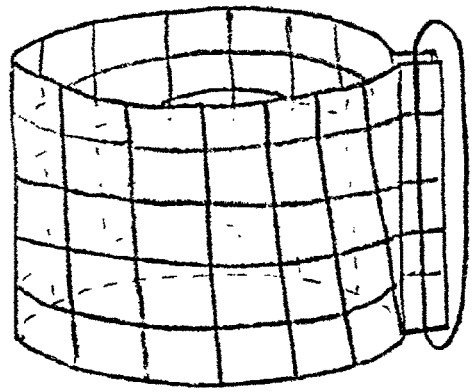
FIG. 8—the same as FIG. 7, with splicing ends of a blank in the form of strip.
Figure 9:
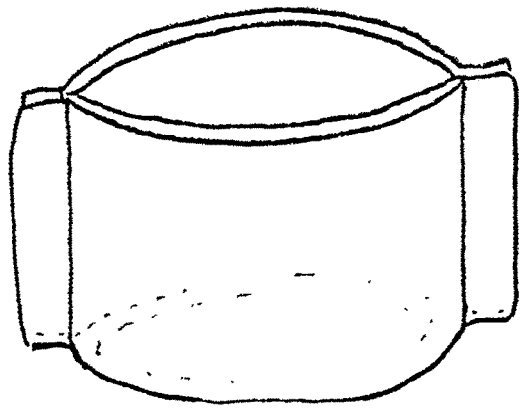
FIG. 9—drainage device made from two blanks in the form of strip by connecting the ends.
Figure 10:
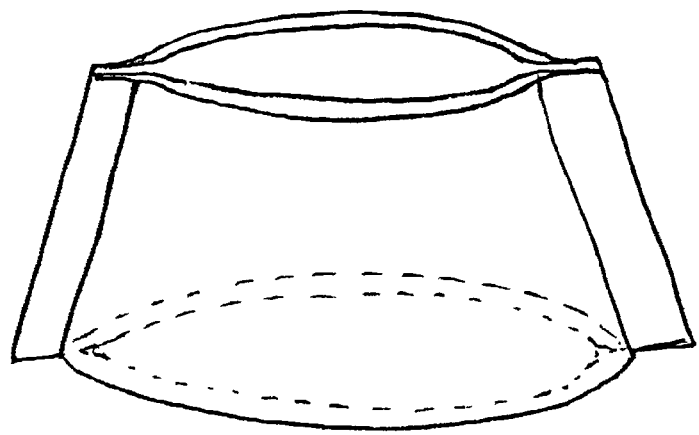
FIG. 10—the same as FIG. 9, with conical side wall.
Figure 11:
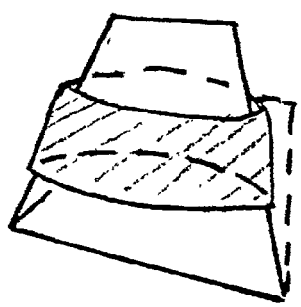
FIG. 11—drainage device on a scleral flap.

Using of one stripe is better in drainage producing because of forming only one stitch (FIG. 6). Two-stitch making is less preferably, because eye tissues may be traumatized (FIG. 10). Due to the same reason lattice cutting along the lateral thread without staring thread offcuts is desired. Fusing of staring thread offcuts is also used.

Not only rectangular, but also trapezoidal with one or two sides are produced in method with preformed stripes. It is convenient for slipping over trapezoidal scleral flap.

This patent deals with synthetic or microbiologically synthesized bioresorbable polymer materials, which are widely used for manufacturing surgical sutures, implants, matrixes for cell engineering and permitted for medical use by FDA (U.S. Food and Drug Administration).

Types of bioresorbable materials used:
synthetic polymers—polyesters on the base of hydroxyalkylcarboxylic (hydroxycarboxylic) acid, their copolymers or mixes, including polyglycolic acid (polyglycolide), L- or D,L-polylactic acid (polylactide), poly-ε-caprolactone, poly-p-dioxanone. Molar ratio of both components in copolymer is called.
synthetic polymers—polyvinyl alcohol hydrogel or a graft-copolymer with polyvinyl alcohol and polyethylene glycol hydrogel.
microbiologically synthesized polymers—polyesters on the base of L-hydroxyalkylcarboxylic (hydroxycarboxylic) acid (i.e. polyhydroxyalkanoates), or their copolymers, especially poly-3-hydroxybutyrate, poly-3-hydroxyvalerate or poly-4-hydroxybutyrate.
microbiologically synthesized materials—fused spider web proteins spidroin-1 and spidroin-2
natural fibers, especially silk made by transgenic silkworm.

All polyesters from the following list are hydrophobic materials with a sorption less than 2-4 mass % of water. Their use is preferably because of drainages manufactured from these materials don't change their size after implantation. Hydrophilic materials can be also used, if their equilibrium swelling is not too large. Polyvinyl alcohol hydrogels and fused spider web are particularly used.

Drainage resorption time (dispersion, biodegradation) is 1-12 months, preferably 3-6 months. It is determined by its thickness and porosity as well as nature of material used. Time mentioned above is a time of complete material resorption; time of strength characteristics decreasing is much less.

Sterilization of manufactured drainages is carried out by radiation or gas (ethylene oxide) method at standard conditions

Drainage Device Producing by Casting on Rod

Example 1. Device Made by Continuous Film

Resorbable polymer solution in organic solvent is prepared by dissolving 0.70 g of polyglycolic acid (polyglycolide) (intrinsic viscosity 1.4 dl/g, PURAC biomaterials) in 9.3 g of freshly distilled hexafluoroisopropanol (7.0 mass. % solution). Polished brassy rod 3.0 mm in diameter and 12.0 cm in height is immersed into a solution, then a rod with cover is dried upright at 40° C. for 60 minutes. After drying a thin tube (hose) shape cover 7.0 cm in length and with wall thickness 40 μm is removed. This polymer tube is dried into a vacuum oven at 35° C. for 2 hours to complete removing of residual solvent. Then a polymer tube is pressed under a short-term exposure by metal sheet weighing 80 g, on a glass surface. After that pieces with rectangular plan 2.5 mm in length are cut out by sharp metal cutter. The result of these operations is the number of drainages 2.5 mm in length, 5.3 mm in width and 80 μm in general thickness, in the shape of plain pieces of thin tube (hose). Then drainages are put into a polypropylene blister and asepticized by radiation method (2.5 MPa)

Example 2. Device Made by Porous Film

A base mixture is prepared by adding 2.8 g of micronized sodium chloride (particle size 40-65 μm) to 10 g of L-polylactic acid (poly-L-lactide) (intrinsic viscosity 1.8 dl/PURAC biomaterials) solution (4.0%) in freshly distilled chloroform and then mixed thoroughly. Polished brassy rod 3.3 mm in diameter and 12.0 cm in height is immersed into a suspension for a small time, then a rod with cover is dried upright at 40° C. for 60 minutes. After that a rod with cover is dried into a vacuum oven at 35° C. for 2 hours to complete removing of residual solvent. Later a rod with cover is placed into a beaker with distilled water and heated into a vacuum oven at 60° C. for 10 hours to complete filler outwashing. Then a rod with cover is dried at 80° C. for 2 hours and after that a thin elastic tube (hose) 7.0 cm in length and 80 μm in general wall thickness is removed from rod. Next a tube is cut out as in example 1. As a result, drainages 2.5 mm in length, 5.5 mm in width and 160 μm in general thickness, in the shape of plain pieces of thin tube (hose) are produced.

Example 3

A porous cover is produced from D,L-polylactic acid (poly-D,L-lactide) solution (intrinsic viscosity 0.70 dl/g, DURECT Corp.) in acetone in the context of Example 2.

Example 4

A porous cover is produced from poly(D,L-lactide-co-glycolide) copolymer solution 50:50 mol. % (intrinsic viscosity 0.70 dl/g, DURECT Corp.) in ethylacetate in the context of Example 2.

Example 5

A porous cover is produced from poly(L-lactide-co-glycolide) copolymer solution 85:15 mol. % (intrinsic viscosity 2.30 dl/g, DURECT Corp.) in tetrahydrofurane in the context of Example 2.

Example 6

A porous cover is produced from poly(D,L-lactide-co-ε-caprolactone) copolymer solution 25:75 mol. % (intrinsic viscosity 0.80 dl/g, PURAC biomaterials) in dioxane in the context of Example 2.

Example 7

A porous cover is produced from poly(D,L-lactide-co-ε-caprolactone) copolymer solution 80:20 mol. % (intrinsic viscosity 0.70 dl/g, PURAC biomaterials) in dioxane in the context of Example 2.

Example 8

A porous cover is produced from poly-ε-caprolactone solution (intrinsic viscosity 0.70 dl/g, DURECT Corp.) in chloroform in the context of Example 2.

Example 9

A porous cover is produced from poly-p-dioxanone solution (intrinsic viscosity 0.85 dl/g) in hexafluoroisopropanol in the context of Example 2.

Example 10

A mix of two solutions is prepared: a first solution is 5.0 g of poly(L-lactide-co-glycolide) copolymer 85:15 mol % (intrinsic viscosity 2.30 dl/g, PURAC biomaterials) solution (4.0%) in freshly distilled chloroform and a second solution is 5.0 g of poly-ε-caprolactone (intrinsic viscosity 0.70 dl/g, PURAC biomaterials) solution (4.0%) in freshly distilled chloroform. Then 2.8 g of micronized sodium chloride (particle size 40-65 μm) is added to solution Prepared system is mixed thoroughly. A porous cover and drainage are produced in the context of Example 2.

Example 11

A porous cover is produced from poly-3-hydroxybutirate solution (intrinsic viscosity 0.46 dl/g) in chloroform in the context of Example 2.

Example 12

A porous cover is produced from poly-3-hydroxyvalerate solution (intrinsic viscosity 0.53 dl/g) in chloroform in the context of Example 2.

Example 13

A porous cover is produced from poly-4-hydroxybutirate solution (intrinsic viscosity 0.49 dl/g) in chloroform in the context of Example 2.

Example 14

A porous cover is produced from poly-(3-hydroxybutirate-co-4-hydroxybutirate) copolymer solution (intrinsic viscosity 0.73 dl/g) in chloroform in the context of Example 2.

Example 15

4.5 g of micronized polyethylene glycol ($M_n$ 10000, particle size 70-90 μm), used as a porophore, is added to a 15.0 g of poly(3-hydroxybutirate-co-3-hydroxyvalerate) (intrinsic viscosity 0.58 dl/g) copolymer solution (5.0%) in freshly distilled chloroform and then mixed thoroughly. Polished brassy rod 3.0 mm in diameter and 12.0 cm in height is immersed into a suspension for a small time, then a rod with cover is dried upright at 40° C. for 60 minutes. After that a rod with cover is dried into a vacuum oven at 35° C. for 2 hours to complete removing of residual solvent. Later a rod with cover is placed into a beaker with distilled water and heated into a vacuum oven at 50° C. for 16 hours to complete filler outwashing. Then a rod with cover is dried at 80° C. for 2 hours and after that a thin elastic tube (hose) 7.0 cm in length and 70 µm in general wall thickness is removed from rod. Next a tube is cut out as in example 1. As a result, drainages 2.0 mm in length, 5.2 mm in width and 140 µm in general thickness, in the shape of plain pieces of thin tube (hose) are produced.

Example 16

A device is made from spidroin according to following steps. Weight quantity of 0.3 g recombinant spidroin-1 is dissolved in 4.0 ml of lithium chloride solution (10%) in 90% formic acid. Then 0.9 g of sodium chloride (particle size 40-65 µm) is added to prepared solution. Polished brassy rod 3.4 mm in diameter is covered with a suspension, then a rod with cover is dried at 40° C. for 3 hours. Then a rod with coat is kept in ethanol 96% for 2 hours, in distilled water for another 2 hours and next is dried into a vacuum oven at 40° C. for 3 hours. A prepared tube is removed from rod, dried and cut out as in example 2.

Example 17

A cover is produced from recombinant spidroin-2 in the context of Example 16.

Example 18. Drainage Device Made of Continuous Film with Flexibilizer 0.29 g of glutardialdehyde water solution (25%) and 0.36 g of glycerin are added to 30.0 g of polyvinyl alcohol water solution (4.0%) ($M_w$ 85 000, 96% of hydrolyzed groups, Aldrich). Polished rod is covered with a prepared solution in the context of Example 1, and then it is placed into a dryer and baking at 60° C. for 3 hours and later 90° C. for 1 hour. A prepared cover is removed from rod and cut out as in example 1.

Example 19

0.52 g of glutardialdehyde water solution (25%) and 0.52 g of glycerin are added to 35.0 g of polyvinyl alcohol and polyethylene glycol graft-copolymer (PVA 75%, PEG 25%, Mw 45000, Kollicoat IR, BASF) water solution (5.0%) ($M_w$ 85 000, 96% of hydrolyzed groups, Aldrich). Polished rod is covered with prepared solution in the context of Example 1, then it is placed into a dryer and baking at 60° C. for 3 hours and later 90° C. for 1 hour. A prepared cover is removed from rod and cut out as in example 1.

Drainage Device Producing by Casting on Cone

Example 20

Polished brassy rod in a form of conoidal frustum 3.4 mm in diameter of upper base, 6.6 mm in diameter of lower base and 10.0 mm in height is covered with a suspension prepared in the context of Example 2. Then a centre of a prepared cover is cut out to obtain a isosceles trapezoid plan 3.5 mm in height, 4.5 mm in lower base, 5.5 mm in upper base and 155 µm in general thickness.

Drainage Device with Lattice Wall Producing by Casting on Rod

Example 21

A poly(glycolide-co-L-lactide) 90:10 mol. % (Vicryl, Johnson and Johnson) thread 35 µm in thickness is wound on a brassy rod 3.2 mm in diameter at an angle of 30° to rod axis at 0.5 mm interval and then backward. After that a rod with cover is dried into an oven at 190° C. for 3 minutes hours, than cooled and placed into distilled water. A prepared tube with lattice wall is removed from a rod, dried at 80° C. and cut across the center. Lattice drainage devices produced by this method are 2.5 mm in height, 5.2 mm in width and 155 µm in thickness.

Drainage Device with Perforated Wall Producing

Example 22

A continuous polymer tube is prepared in the context of Example 1 and then pressed under a short-term exposure by metal sheet on a glass surface. Subsequent perforation is carried out by laser Excimer, ATL (5 W, 5 ns, 300 Hz). Pores 200 µm in diameter are made in to staggered order at 400 µm interval. Then drainage devices are cut out in the context of Example 1.

Example 23

Perforation is carried out by dermatome D42, Humeca in the context of Example 22. Through-thickness cuttings with 1.0*1.0 mm pores are made in staggered order. Then drainage devices are cut out in the context of Example 1.

Drainage Device Woven from Thread

Example 24

A hose 30 cm in length and 5.5 mm in inner diameter is woven from a poly(glycolide-co-L-lactide) 90:10 mol. % (Vicryl, Johnson and Johnson) thread 30 µm in thickness. The hose is cut out to several drainages and its edges are processed for threads fixing by using 2-octylcyanoacrylate glue <<Dermabond>>, Johnson and Johnson. Drainage devices produced by this method are 3.0 mm in height, 5.2 mm in width and 130 µm in thickness.

Drainage Device Producing from Stripe Blanks

Example 25

A mixture obtained in the context of Example 1 is poured out on a horizontal glass plate. After a solvent evaporation at room temperature, a film is dried on a plate at 40° C. for 60 minutes. Then a film is dried into a vacuum oven at 35° C. for 2 hours to complete removing of residual solvent. Later a film is removed from a plate and placed into a beaker with distilled water and heated into a vacuum oven at 60° C. for 10 hours to complete filler outwashing. Then a film is dried at 80° C. for 2 hours. The porous film is cut into stripes 2.5 mm in weight (or height in drainage device) and these stripes are cut into pieces 11.2 mm in length. Porous blanks are doubled up and processed by thermal welding at 180° C. by using a polymer welding device CT-320, CT Brand. Weld thickness is 0.6 mm. Drainage devices produced by this method are 2.5 mm in height, 5.6 mm in width and 180 μm in thickness.

Example 26

Blank stripes obtained in the context of Example 25 are welded with an angle to produce one-sided trapezoid in plan. Weld thickness is 0.6 mm in this case. Trapezoid drainages are 2.5 mm in height, upper base 5.6 mm, lower base 2.5 mm and 180 μm in thickness after removing an indirect corner Example 27

Blank stripes obtained in the context of Example 25 are doubled up and ends are glued by using 2-octylcyanoacrylate glue <<Dermabond>>, Johnson and Johnson. A bonded seam thickness is 0.6 mm. Drainage devices produced by this method are 2.5 mm in height, 5.6 mm in width and 180 μm in thickness.

Example 28

Blank stripes obtained in the context of Example 25 are doubled up and ends are glued by using cyanoacrylate glue <<Permabond>>4UV80HV, Ellsworth Adhesives after UV-lamp impact (4 mW/cm$^2$). Time of glue fixing is 10 minutes. A bonded seam thickness is 0.6 mm. Drainage devices produced by this method are 2.5 mm in height, 5.6 mm in width and 180 μm in thickness.

Example 29

10.0 g of D,L-polylactic acid (poly-D,L-lactide) (intrinsic viscosity 0.70 dl/g, DURECT Corp.) solution (4.0%) in freshly distilled tetrahydrofurane is prepared. Then a solution is poured out on a horizontal glass plate. After a solvent evaporation at room temperature, a film is dried on a plate at 40° C. for 60 minutes. Then a film is dried into a vacuum oven at 35° C. for 2 hours to complete removing of residual solvent. Later a film is removed from a plate and placed into a beaker with distilled water and heated into a vacuum oven at 60° C. for 10 hours to complete filler outwashing. Then a film is dried at 80° C. for 2 hours. This continuous film 80 μm in thickness is perforated by laser in the context of Example 22, then it is cut into stripes 2.5 mm in width (or height in drainage device) and these stripes are cut into pieces 11.2 mm in length. Porous blanks are doubled up and processed by thermal welding at 140° C. by using a polymer welding device CT-320, CT Brand. Weld thickness is 0.4 mm. Drainage devices produced by this method are 2.5 mm in height, 5.6 mm in width and 160 μm in thickness.

Example 30

A continuous film is produced in the context of Example 29. Than it is perforated by dermatome in the context of Example 23, and a film is cut into stripes 3.0 mm in width (or height in drainage device) and these stripes are cut into pieces 11.4 mm in length. Porous to blanks are doubled up and processed by thermal welding at 140° C. by using a polymer welding device CT-320, CT Brand. Weld thickness is 0.3 mm. Drainage devices produced by this method are 3.0 mm in height, 5.7 mm in width and 160 μm in thickness.

Example 31

Reabsorbed lattice Vicryl, Johnson and Johnson made from poly (glycolide-co-L-lactide) 90:10 mol. % 180 μm in thickness with quite square pores 500*500 is used. Then a film is cut out along lattice forming threads stripes 3.0 mm in width (or height in drainage device) and 11.0 mm in length. Sharp cut off threads shouldn't stick up on end. These blanks are doubled up and processed by thermal welding at 190° C. by using a polymer welding device CT-320, CT Brand. Weld thickness is 0.5 mm. Drainage devices produced by this method are 2.5 mm in height, 5.5 mm in width (with a weld edge) and 360 μm in thickness.

Example 32

Blanks obtained in the context of Example 31 are doubled up and spliced along the drainage axis by poly(glycolide-co-L-lactide) 90:10 mol. % (Vicryl, Johnson and Johnson) thread 35 μm in thickness. Drainage devices produced by this method are 2.5 mm in height, 5.5 mm in width (with a spliced edge) and 360 μm in thickness.

Example 33

Blanks are doubled up and both ends are spliced by poly(glycolide-co-L-lactide) 90:10 mol. % (Vicryl, Johnson and Johnson) thread 35 μm in thickness. A thread is spliced only end lattice threads. In this case a connection without staring elements (as in a method with using rod) is obtained. It is more preferable because a device is free of staring elements, which can lead to tissue diseases. Drainage devices produced by this method are 2.5 mm in height, 5.5 mm in width (with a spliced edge) and 360 μm in thickness.

Example 34

A porous film blank 90 μm in thickness is obtained in the context of Example 25. Then a film is cut into stripes 2.5 mm in width (or height in drainage device) and these stripes are cut into pieces 5.5 mm in length. Porous blanks are overlayed by each other and processed by thermal welding at 180° C. by using a polymer welding device CT-320, CT Brand. Weld thickness is 0.4 mm. Drainage devices produced by this method are 2.5 mm in height, 5.5 mm in width and 180 μm in thickness.

Example 35

A porous film blank 90 μm in thickness is obtained in the context of Example 25. Then a film is cut into stripes 2.5 mm in width (or height in drainage device) and these stripes are cut into pieces 5.5 mm in length. Porous blanks are overlayed by each other and processed by thermal welding at 180° C. with obtaining a double-sided trapezoid by using a polymer welding device CT-320, CT Brand. Weld thickness is 0.4 mm. Drainage devices produced by this method are 2.5 mm in height, 5.4 mm in upper base, 3.8 mm in lower base and 180 μm in thickness after removing an indirect corners.

Drainage devices produced by these methods are tested in human trials to treat glaucoma.

Patient S., 74 y/o M/R #844.11, was admitted to the hospital with the diagnosis OS—II-III C glaucoma, operated two times, initial cataract, OD—open-angle II A glaucoma, initial cataract. From anamnesis in 2001 there was antiglaucomatous operation on the OS, and then repeated antiglaucomatous operation was performed in 2005. At admission to the hospital tonometric pressure of the left eye was 32 mm Hg on the maximal antoglaucomatous regimen. In the area of filtering bleb rough cicatrical changes are observed. Taking into account the clinical picture, it was decided to carry out surgical treatment of glaucoma (penetrating antiglaucomatous operation). Separation of the limbus-based conjunctival flap was performed. Superficial trapezoid scleral flap with large base in the area of the limb by ½ of its thickness, 5 mm in length, with the lesser base of the trapezium 3 mm, on 13 hrs, was formed, considering rough cicatrical changes from the previous operation. Location of the drainage device around the scleral flap with preliminarily modeled proper sizes of the drainage was the next step. Deep stripe of the sclera with the trabecular tissue was cut out and excised in the limbal area. Basal iridectomy was carried out. Reposition of the scleral flap with the nodal stitch in the area of the apex and two nodal stitches at the base of the scleral flap was performed. Antiglaucomatous operation was completed with reposition of the conjunctival flap and continuous suture. At discharge from the hospital the pressure by palpation was within norm, the filtering bleb was moderately expressed and it functioned well. At repeated examination 1.5 months after the operation intraocular pressure was 19 mm Hg, the filtering bleb functioned well; according to the data of ultrasound biomicroscopy preservation of the implantable material was marked. At the examination 3 months after the operation the filtering bleb was flat, intraocular pressure was Po-12 mm Hg. According to the data of ultrasound biomicroscopy preservation of the implantable material was marked. 6 months after the operation intraocular pressure—Po was 12 mm Hg; according to the data of ultrasound biomicroscopy preservation of the implantable material was confirmed. At the examination 9 months after the operation stable IOD at the level of 13 mm Hg without disturbance of the visual functions was preserved; according to the data of ultrasound biomicroscopy complete resolution of the implantable material was confirmed.

Patient A., 80 y/o M/R #2481.11, was admitted to the hospital with the diagnosis OS—open-angle III B glaucoma, immature cataract, OD—open-angle III A glaucoma, initial cataract, OU—high degree myopia. From anamnesis: myopia has presented since childhood, glaucoma was diagnosed about 3 years ago. At admission to the hospital tonometric pressure in the lift eye was 26 mm Hg on maximal antiglaucomatous regimen. Considering the clinical picture, the decision to carry out surgical treatment of glaucoma (non-penetrating antiglaucomatous operation) was made. Separation of the limbus-based conjunctival flap was carried out. Formation of the limbus-based superficial trapezoid scleral flap by ½ of its thickness, 4 mm in size at the base and 2 mm at the top of the trapezium was performed. Location of the drainage device around the scleral flap, with preliminarily modeled proper sizes of the drainage was the next step. Removal of middle layers of the sclera in the form of a rectangle till the internal layers of the corneoscleral part of the trabecula and the limbal edge of the Decemet's membrane was carried out. Reposition of the scleral flap with the nodal stitches placed at the apex area was performed. Antiglaucomatous operation was completed by reposition of the conjunctival flap with continuous suture. At discharge from the hospital the pressure at palpation was within norm; the filtrating bleb was moderately expressed and it functioned well. At repeated examination 1.5 months after the operation intraocular pressure Po was 12 mm Hg, the filtrating bleb functioned well; according to the data of ultrasound biomicroscopy preservation of the implantable material was marked. At examination 3 months after the operation the filtrating bleb was flat, Po was 14 mm Hg.

According to the data of ultrasound biomicroscopy preservation of the implantable material was marked. 6 months after the operation the intraocular pressure—Po was 13 mm Hg; according to the data of ultrasound biomicroscopy complete resorption of the implantable material was confirmed.

Application of the claimed drainage is possible together with mini-shunt Ex-PRESS. It is necessary to perform the technique of the operation according to the following algorithm. Separation of the conjunctival flap with its base towards to the limb or from the limb. Formation of the limbus-based superficial trapezoid scleral flap by ½ of its thickness, 4 mm in size at the base and 2 mm—at the top. Location of the drainage device around the scleral flap with preliminarily modeled proper sizes of the drainage. Implantation of the mini-shunt Ex-PRESS. Reposition of the scleral flap with the nodal stitch, placed at the apex. Completion of the antiglaucomatous operation with reposition of the conjunctival flap with continuous suture. This operation allows to save the flow of aqueous humor and to prevent the obliteration of the way of outflow from the mini-shunt.

Specified method of performing the operation and the claimed drainage devices are gestated in the Ophthalmological clinical hospital on 112 patients, which underwent antiglaucomatous operation with placement of the drainage devices according to the invention. The average terms of observation were 12 months. In all cases intraocular pressure was within norm; there was no cicatrical changes in the area of the filtering bleb and the scleral flap, the filtering bleb was flat, it completely performed its function.

In conclusion it is important to note that the above-described examples of realization of the invention shouldn't be explained as the only possible and confining the scope of requesting legal protection, which is defined solely by the appended claim.

INDUSTRIAL APPLICABILITY

The invention can be applied in medicine in surgical service of different types of glaucoma (primary, obstinate, repeated operative treatment, complicated cases in repeated glaucoma).

The invention claimed is:

1. A drainage device used in the surgical treatment of glaucoma, formed from a bioresorbable material in the form of a hollow profile with a closed contour in cross section, the device having a size and form configured to allow a scleral flap, separated during a surgical treatment, to pass through a cavity of the device.

2. The device according to claim 1, produced in the form of a thin-walled tube, outer surface of which is constructed in the form of a closed cross section with a tubular or conical shape.

3. The device according to claim 2, in which the specified thin-walled tube is folded flat.

4. The device according to claim 3 with a rectangular plan 4.0-6.0 mm in width and 1.5-3.5 mm in height, and a device thickness of 10-500 μm.

5. The device according to claim 3 with a trapezoidal plan 4.0-6.0 mm across the longer side and 2.5-5.5 mm across the smaller side, 1.5-3.5 mm in height, and a device thickness of 10-500 µm.

6. The device according to claim 1, made of film.

7. The device according to claim 6, made of porous film.

8. The device according to claim 6, made of at least partially perforated film.

9. The device according to claim 1 with a lattice wall.

10. The device according to claim 1, made of bioresorbable material selected from the group consisting of synthetic materials and microbiologically synthesized materials.

11. The device according to claim 10, made of synthetic polymer selected from the group consisting of: polyglycolic acid (polyglycolide), L- or D,L-polylactic acid (polylactide), poly-ε-caprolactone, poly-p-dioxanone, copolymers of these materials, mixes of these materials, and combinations thereof.

12. The device according to claim 10, made of synthetic polymer polyvinyl alcohol or polyvinyl alcohol and polyethylene glycol graft-copolymer hydrogel.

13. The device according to claim 10, made of microbiologically synthesized material selected from the group consisting of: poly-3-hydroxybutyrate, poly-3-hydroxyvalerate, poly-4-hydroxybutyrate, and their copolymers.

14. The device according to claim 10, made of microbiologically synthesized materials from spider web proteins spidroin-1 and spidroin-2.

15. A method for producing a drainage device according to claim 1 produced by manufacturing a blank from polymer material on a rod in the form of a hollow profile of closed cross section and subsequently cutting at least one section out of the blank in order to produce at least one drainage device.

16. The method of claim 15, wherein a blank is poured from polymer solution.

17. The method of claim 16, wherein a blank wall is perforated fractionally.

18. The method of claim 15, wherein a blank is poured from polymer solution containing a water-soluble addition; the blank is dried and an addition is washed out before cutting out for producing a porous film.

19. The method of claim 15, wherein a blank is manufactured by winding a thread on a rod and later baking to obtaining a tube with a lattice wall.

20. The method of claim 15, wherein a blank in the form of a hollow profile of closed cross section is woven from threads and at least one section is subsequently cut out of the blank in order to produce at least one drainage device.

21. The method of claim 15, wherein blanks in the form of strips are produced from a flat preliminary blank made of polymer material, wherein the drainage device is produced by connecting the ends of at least one blank.

22. The method of claim 21, wherein a blank is poured in the form of a sheet from polymer solution.

23. The method of claim 21, wherein a blank is poured in the form of a sheet from polymer solution containing a water-soluble addition; the blank is dried and an addition is washed out before cutting out for producing a porous film.

24. The method of claim 21, wherein a blank is made of lattice from bioresorbable threads.

25. The method of claim 21, wherein a drainage device is produced by connecting the ends of one or more blanks by high-temperature welding, gluing, or splicing.

* * * * *